United States Patent
Robert et al.

(10) Patent No.: US 8,870,238 B2
(45) Date of Patent: Oct. 28, 2014

(54) FITTING FOR MEDICAMENT INFUSION SYSTEMS

(75) Inventors: Renee Robert, Shoreview, MN (US); Chad Amborn, Minneapolis, MN (US); Geoff Clark, Lempster, NH (US)

(73) Assignee: Smiths Medical ASD, Inc., Rockland, MA (US)

( * ) Notice: Subject to any disclaimer, the term of this patent is extended or adjusted under 35 U.S.C. 154(b) by 0 days.

(21) Appl. No.: 13/517,836

(22) Filed: Jun. 14, 2012

(65) Prior Publication Data

US 2012/0326438 A1  Dec. 27, 2012

Related U.S. Application Data

(60) Provisional application No. 61/573,094, filed on Aug. 31, 2011.

(51) Int. Cl.
 *F16L 21/00* (2006.01)
 *A61M 39/10* (2006.01)

(52) U.S. Cl.
 CPC ..... *A61M 39/1011* (2013.01); *A61M 2205/584* (2013.01); *A61M 2039/1094* (2013.01); *Y10S 604/905* (2013.01)
 USPC ............ 285/401; 285/376; 604/905; 604/533

(58) Field of Classification Search
 USPC ............ 285/396, 38, 390; 604/905, 503, 240, 604/533
 See application file for complete search history.

(56) References Cited

U.S. PATENT DOCUMENTS

| | | | |
|---|---|---|---|
| 1,871,370 A | 8/1932 | Jacques | |
| 2,564,804 A * | 8/1951 | Everett | ............................. 285/38 |
| 3,170,667 A | 2/1965 | Szohatzky | |
| 3,287,031 A | 11/1966 | Simmons et al. | |
| 4,076,285 A | 2/1978 | Martinez | |
| 4,080,737 A | 3/1978 | Fleer | |
| 4,116,476 A | 9/1978 | Porter et al. | |
| 4,137,917 A | 2/1979 | Cohen | |
| 4,150,673 A | 4/1979 | Watt | |
| 4,211,439 A | 7/1980 | Moldestad | |
| 4,280,723 A | 7/1981 | Moldestad | |

(Continued)

FOREIGN PATENT DOCUMENTS

| | | |
|---|---|---|
| EP | 217055 | 4/1987 |
| EP | 774270 | 5/1997 |

(Continued)

OTHER PUBLICATIONS

Chinese Office Action issued Apr. 6, 2012 re: CN Appln No. 2011101192607.

(Continued)

*Primary Examiner* — David E Bochna

(74) *Attorney, Agent, or Firm* — Louis Woo

(57) ABSTRACT

A female connector for medical infusion systems has a main body that has two curved wings that extend from the outer circumferential surface of the body. The respective front ends of the wings are joined integrally to a substantially circumferential partition that also extends circumferentially from the outer circumferential surface of the fitting. The connector of the fitting has a non-conventional configuration with at least two protuberances offset at an angle. The non-conventional configuration of the connector allows the fitting to only mate with a counterpart connector that has a complementary non-conventional configuration.

11 Claims, 1 Drawing Sheet

(56) References Cited

U.S. PATENT DOCUMENTS

| | | | |
|---|---|---|---|
| 4,294,250 A * | 10/1981 | Dennehey | 604/905 |
| 4,452,473 A | 6/1984 | Ruschke | |
| 4,453,927 A | 6/1984 | Sinko | |
| 4,619,640 A | 10/1986 | Potoisky | |
| 4,682,981 A | 7/1987 | Suzuki et al. | |
| 4,758,225 A | 7/1988 | Cox et al. | |
| 4,790,567 A | 12/1988 | Kawano et al. | |
| 4,940,458 A | 7/1990 | Cohn | |
| 5,069,225 A | 12/1991 | Okamura | |
| 5,348,048 A * | 9/1994 | Schirado et al. | 285/361 |
| 5,393,101 A | 2/1995 | Matkovich | |
| 5,405,339 A | 4/1995 | Kohnen et al. | |
| 5,405,340 A | 4/1995 | Fageol et al. | |
| 5,538,399 A | 7/1996 | Johnson | |
| 5,545,152 A | 8/1996 | Funderburk et al. | |
| 5,562,121 A | 10/1996 | Hodges et al. | |
| 5,591,143 A | 1/1997 | Trombley, III et al. | |
| D378,130 S | 2/1997 | Schmidt | |
| 5,605,359 A | 2/1997 | Hoff | |
| D378,405 S | 3/1997 | Musgrave et al. | |
| 5,616,133 A | 4/1997 | Cardenas | |
| 5,620,427 A | 4/1997 | Werschmidt et al. | |
| 5,632,735 A | 5/1997 | Wyatt et al. | |
| 5,651,776 A | 7/1997 | Appling et al. | |
| 5,688,254 A | 11/1997 | Lopez et al. | |
| 5,695,473 A | 12/1997 | Olsen | |
| 5,725,511 A | 3/1998 | Urrutia | |
| 5,741,084 A | 4/1998 | Del Rio et al. | |
| 5,741,269 A | 4/1998 | McCredy | |
| 5,749,861 A | 5/1998 | Guala et al. | |
| 5,782,505 A * | 7/1998 | Brooks et al. | 604/533 |
| 5,810,398 A | 9/1998 | Matkovich | |
| 5,853,391 A | 12/1998 | Bell | |
| 5,855,230 A | 1/1999 | Guala et al. | |
| 5,925,028 A | 7/1999 | Delvigo | |
| 5,947,937 A | 9/1999 | Urrutia et al. | |
| D417,733 S | 12/1999 | Howell et al. | |
| D421,119 S | 2/2000 | Musgrave et al. | |
| 6,027,480 A | 2/2000 | Davis et al. | |
| 6,156,025 A | 12/2000 | Niedospial et al. | |
| 6,171,281 B1 | 1/2001 | Zhang | |
| 6,197,007 B1 | 3/2001 | Thorne et al. | |
| 6,244,632 B1 | 6/2001 | Gasparini | |
| 6,309,543 B1 | 10/2001 | Fenton | |
| D452,003 S | 12/2001 | Niermann | |
| D452,314 S | 12/2001 | Niermann | |
| 6,402,207 B1 | 6/2002 | Segal et al. | |
| 6,422,607 B1 | 7/2002 | Kirby | |
| 6,428,514 B1 | 8/2002 | Goebel et al. | |
| 6,475,190 B2 | 11/2002 | Young | |
| 6,500,153 B1 | 12/2002 | Sheppard et al. | |
| 6,506,181 B2 | 1/2003 | Meng et al. | |
| 6,511,472 B1 | 1/2003 | Hayman et al. | |
| D469,870 S | 2/2003 | Niermann et al. | |
| 6,536,805 B2 | 3/2003 | Matkovich | |
| 6,558,353 B2 | 5/2003 | Zohmann | |
| 6,612,624 B1 | 9/2003 | Segal et al. | |
| 6,656,161 B2 | 12/2003 | Young et al. | |
| 6,688,651 B2 | 2/2004 | Min-cheol | |
| 6,722,705 B2 | 4/2004 | Korkor | |
| 6,786,131 B2 | 9/2004 | Tsai | |
| 6,802,836 B2 | 10/2004 | Bouphavichith et al. | |
| 6,843,513 B2 | 1/2005 | Guala | |
| 6,893,056 B2 | 5/2005 | Guala | |
| 6,953,448 B2 | 10/2005 | Moulton et al. | |
| 6,988,423 B2 | 1/2006 | Bolam et al. | |
| 7,115,228 B2 | 10/2006 | Lundtveit et al. | |
| 7,240,927 B2 | 7/2007 | Chang | |
| 7,270,349 B2 | 9/2007 | Bamberger et al. | |
| 7,641,648 B2 | 1/2010 | Bouphavichith et al. | |
| 7,857,805 B2 | 12/2010 | Raines | |
| 7,955,315 B2 | 6/2011 | Feinberg et al. | |
| 8,343,138 B2 * | 1/2013 | Asfora | 604/540 |
| 8,372,057 B2 * | 2/2013 | Cude et al. | 604/533 |
| 2001/0049490 A1 | 12/2001 | Slanda et al. | |
| 2003/0105428 A1 | 6/2003 | Hogan et al. | |
| 2004/0167474 A1 | 8/2004 | Meng et al. | |
| 2004/0201216 A1 | 10/2004 | Segal et al. | |
| 2005/0090801 A1 | 4/2005 | Racz et al. | |
| 2005/0225082 A1 | 10/2005 | Dalle et al. | |
| 2007/0270758 A1 | 11/2007 | Hanner et al. | |
| 2008/0177250 A1 | 7/2008 | Howlett et al. | |
| 2008/0287919 A1 | 11/2008 | Kimball | |
| 2008/0312640 A1 | 12/2008 | Grant | |
| 2009/0187166 A1 | 7/2009 | Young | |
| 2009/0243281 A1 | 10/2009 | Seifert et al. | |
| 2009/0299339 A1 | 12/2009 | Young | |
| 2010/0022951 A1 | 1/2010 | Ferrera et al. | |
| 2010/0094260 A1 | 4/2010 | Cude et al. | |

FOREIGN PATENT DOCUMENTS

| | | |
|---|---|---|
| EP | 1010439 | 6/2000 |
| FR | 2642139 | 7/1990 |
| GB | 771967 | 4/1957 |
| JP | H11-319114 | 11/1999 |
| JP | 2001-187990 | 7/2001 |
| WO | 2005/044335 | 10/2004 |

OTHER PUBLICATIONS

Canadian Office Action issued Apr. 13, 2012 re: CA Appln No. 2575136.

Sheppard et al., "Improving patient safety by design—a new spinal/intrathecal injection safety system", Can J Anesth 2006; 0108-9.

* cited by examiner

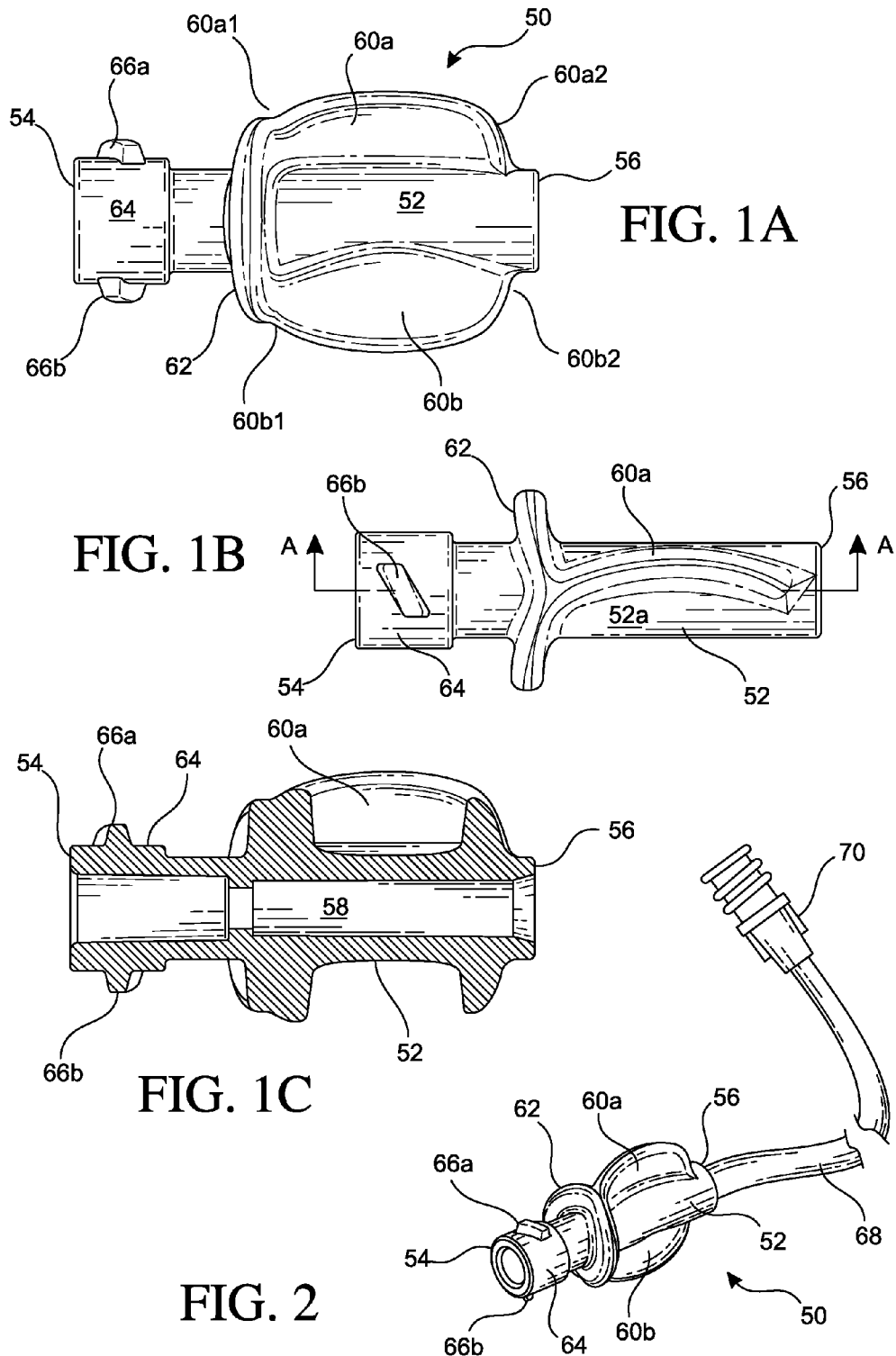

FITTING FOR MEDICAMENT INFUSION SYSTEMS

FIELD OF THE INVENTION

The present invention relates to medication infusion systems, and particularly relates to a fitting that has a connector with features that enable it to be matable only to a counterpart complementary connector and a finger grip configuration that enables a user to readily grasp it.

BACKGROUND OF THE INVENTION

In provisional application Ser. No. 61/457,879 entitled "Medicament Infusion Systems", there is disclosed, among other things, an exemplar special connector of a drug delivery system. The fitting of the instant invention is an alterative embodiment of the special connector.

SUMMARY OF THE PRESENT INVENTION

The fitting of the instant invention comprises a specially configured female connector for a drug delivery system that is an alternative embodiment to a similar female connector disclosed in provisional application No. 61/457,879. The disclosure of U.S. 61/457,879 is incorporated by reference to this application.

The fitting of the instant invention includes a substantially cylindrical body having a proximal end and a distal end. A through passage is established between the two ends so that fluid may traverse through the fitting. There are two wings integrally extending from the outer circumferential wall of the body. The respective front ends of the wings are joined to a substantially circumferential partition wall that extends away from the outer circumferential surface of the body at a location along the body so that a shielded grasping configuration is provided for the fingers of a user, when the user grasps the fitting with his fingers. At the proximal end of the fitting fore of the partition wall there is a connector of a special non-conventional configuration that enables the connector to only mate with a counterpart connector having a non-conventional complementary configuration. The special configuration at the connector may include two protuberances, or tabs, formed at an angle offset from the longitudinal axis of the fitting. The connector may also have a tapered opening that prevents it from mating with a conventional counterpart connector. The distal end of the fitting may have fixedly attached thereto a tubing whose other end may be fitted with a conventional connector for connection to a fluid store so that fluid may be conveyed between the fluid store and the fitting.

BRIEF DESCRIPTION OF THE FIGURES

The instant invention will be best understood with reference to the following drawings, wherein:

FIG. 1*a* is a side view of the connector fitting of the instant invention;

FIG. 1*b* is a top view of the FIG. 1*a* fitting;

FIG. 1*c* is a cross-sectional view along line A-A of the fitting shown in FIG. 1*b*; and FIG. 2 is a perspective view of the fitting of the instant invention shown having attached to its other end a tubing.

DETAILED DESCRIPTION OF THE INVENTION

With reference to the FIGS. 1*a*-1*c* and 2, fitting 50 may be a female CORRECTINJECT® (CI) connector to be used with a computerized ambulatory drug delivery (CADD) system, per disclosed in the incorporated by reference '879 application. As shown, fitting 50 has a substantially cylindrical body 52 having a proximal end 54 and a distal end 56. A through passage 58 connects ends 54 and 56.

Two wings 60*a* and 60*b*, formed integrally from the body 52, extend outwardly from the outer circumferential surface 52*a* of body 52. Wings 60*a* and 60*b* each have a front end and a back end. The front end and back end of wing 60*a* are designated 60*a*1 and 60*a*2, respectively. The front end and back end of wing 60*b* are designated 60*b*1 and 60*b*2, respectively. Wing 60*a* curves inwardly into the paper, with reference to FIG. 1*a*, and its curvature can best be seen in the top plan view of FIG. 1*b* and also the perspective view of FIG. 2. Wing 60*b*, on the other hand, has an outward curvature, with reference to the paper, that points towards the reader. Wing 60*b* therefore curves in the opposite direction as wing 60*a*. The respective curvatures of wings 60*a* and 60*b* enable a user to better grasp fitting 50 with his fingers, for example his forefinger and thumb.

Fitting 50 further has a substantially circumferential partition wall 62 that extends away from the outer circumferential surface 52*a* of body 52. Wall 62 is joined integrally to the respective front ends 60*a*1 and 60*b*1 of wings 60*a* and 60*b*. As best shown in FIGS. 1*b* and 2, both half portions of wall 62 that are orthogonal but not joined to the respective front ends of wings 60*a* and 60*b* are slightly bent or curved towards connector 64 of the fitting and form a shield for the fingers of the user, when the user grasps wings 60*a* and 60*b*, and body 52, with his fingers. Wall 62 prevents the fingers of the user from inadvertently making contact with connector 64 of fitting 50 and in particular end 54 thereof, so as to prevent possible contamination of the fluid path.

There are two tabs, or protuberances 66*a* and 66*b*, at connector portion 64. These protuberances are formed at an offset angle relative to the longitudinal axis of the fitting. The longitudinal axis of the fitting may be considered to lie along the cross-sectional line A-A. With protuberances 66*a* and 66*b* formed thereon, connector 64 is matable only with a counterpart connector that has a complementary configuration. Connector 64 may moreover have the same dimensional features as those disclosed in the '879 application for the connector of FIGS. 4*a*-4*c* and 5. Thus, connector 64 is not connectable to conventional counterpart connectors that are manufactured in accordance with ISO (International Standard Organization) standards such as ISO 594-1 and 594-2.

Although discussed as having various components, it should be appreciated that fitting 50 may be molded as an integral single unitary piece, using conventional medical plastics material such as, not to be limiting, polyvinyl chloride (PVC) and other types of polymers. For distinctiveness, so that a user can readily ascertain that the fitting is a female CI connector that is connectable to a counterpart male CI connector with complementary features, fitting 50 may be molded to have a particular color such as yellow.

FIG. 2 shows in perspective fitting 50. As shown, a tubing 68 may be fixedly attached to end 56 of the fitting. The other end of tubing 68 may be directly attached to a fluid reservoir such as the cassette fluid store disclosed in the '879 application, as for example by bonding, gluing, or other well known attachment methods. In place of a direct connection, the other end of tubing 68 may be fitted with a connector 70 that is connectable to a counterpart connecter at the fluid store. When tubing 68 is in fluid communication with the fluid store, medicament and/or other fluids may traverse between fitting 50 and the fluid store.

The invention claimed is:

1. A fitting comprising:
   a substantially cylindrical body having a proximal end, a distal end and a first outer circumferential surface, a connector at the proximal end having a second outer circumferential surface that has a larger circumference than the first outer circumferential surface, a through passage connecting the proximal and distal ends;
   a substantially circumferential partition wall having a circumference larger than the circumference of the second outer circumferential surface extending orthogonally away from the first outer circumferential surface of the body at a location away from the second circumferential surface of the connector so that a given portion of the cylindrical body having the first outer circumferential surface separates the connector from the partition wall;
   two wings integrally extending from the first outer circumferential surface of the body with respective front ends in the direction of the proximal end joined to the partition wall and respective rear ends of the wings towards the distal end of the body integrally merge to the body;
   wherein the connector is a non-conventional connector at the proximal end of the body, the connector including at least two protuberances extending away from the second outer circumferential surface and formed at an angle offset from the longitudinal axis of the body away from the proximal end, the non-conventional connector adapted to mate only with a complementary non-conventional connector, the non-conventional connector not matable with a conventional connector manufactured in accordance with ISO (International Standard Organization) standards.

2. Fitting of claim 1, wherein the wings are curved in opposite directions relative to each other along the length of the body.

3. Fitting of claim 1, wherein the portions of the circumferential partition wall not joined to the respective front ends of the wings are slightly curved toward the connector to form a shield to prevent the fingers of the user from coming into contact with the connector.

4. Fitting of claim 1, further comprising a tubing having one end fixedly attached to the distal end of the body, another connector fixedly attached to the other end of the tubing, the another connector connectable to a counterpart connector at a fluid store.

5. Fitting of claim 1, wherein the fitting is colored yellow.

6. Fitting of claim 1, further comprising a tubing having one end fixedly attached to the distal end of the body and another end connected to a fluid store.

7. A fitting comprising:
   a substantially cylindrical body having a proximal end, a distal end and a first outer circumferential surface, a connector at the proximal end having a second outer circumferential surface that has a larger circumference than the first outer circumferential surface the proximal and distal ends connected by a through passage;
   two wings integrally extending from the first outer circumferential surface of the body with respective front ends in the direction of the proximal end integrated to a substantially circumferential partition wall that has a circumference larger than the circumference of the second outer circumferential surface, the partition wall extending orthogonally away from the first outer circumferential surface of the body, respective rear ends of the two wings integrally merging to the body and extending towards the distal end of the body;
   wherein the connector at the proximal end of the body is separated from the partition wall and the two wings by a portion of the body having the first outer circumferential surface, the connector having a given configuration matable only to a counterpart connector with a configuration complementary to the given configuration, the connector not connectable to a conventional connector manufactured in accordance with ISO (International Standard Organization) standards;
   a tubing having one end fixedly connected to the distal end of the body and another end having a conventional connector.

8. Fitting of claim 7, wherein the connector comprises two protuberances at an angle offset from the longitudinal axis of the body extending from the second outer circumferential surface away from the proximal end.

9. Fitting of claim 7, wherein the wings are curved in opposite directions relative to each other along the length of the body.

10. Fitting of claim 7, wherein the fitting is colored yellow.

11. Fitting of claim 7, wherein portions of the partition wall not joined to the respective front ends of the wings are slightly curved toward the connector to form a shield to prevent the fingers of a user from coming into contact with the connector.

* * * * *